(12) United States Patent
Quill et al.

(10) Patent No.: US 12,390,329 B1
(45) Date of Patent: Aug. 19, 2025

(54) MEDICAL DEVICE DELIVERY SYSTEMS

(71) Applicant: Anteris Technologies Corporation, Eagan, MN (US)

(72) Inventors: Jason L. Quill, Forest Lake, MN (US); Robert Garryl Hudgins, Monticello, MN (US); Madhulika Srikanth, Minneapolis, MN (US); Christopher William Hummel, Minneapolis, MN (US); Daniel Joe Potter, Stillwater, MN (US); Laura Elyn Ortega, Fridley, MN (US); Joanna Emmanuel Fakhoury, Robbinsdale, MN (US); Alexa Mae Hanneman, Coon Rapids, MN (US); Cameron James Albin Murto, Saint Michael, MN (US); John Albert Adler, Coon Rapids, MN (US)

(73) Assignee: Anteris Technologies Corporation, Eagan, MN (US)

(*) Notice: Subject to any disclaimer, the term of this patent is extended or adjusted under 35 U.S.C. 154(b) by 0 days.

(21) Appl. No.: 19/041,445

(22) Filed: Jan. 30, 2025

Related U.S. Application Data

(60) Provisional application No. 63/554,666, filed on Feb. 16, 2024.

(51) Int. Cl.
| | |
|---|---|
| *A61F 2/24* | (2006.01) |
| *A61F 2/958* | (2013.01) |
| *A61M 25/00* | (2006.01) |
| *A61M 25/01* | (2006.01) |

(52) U.S. Cl.
CPC .... *A61F 2/2433* (2013.01); *A61F 2002/9586* (2013.01); *A61F 2230/0067* (2013.01); *A61M 2025/0004* (2013.01); *A61M 25/0013* (2013.01); *A61M 25/0147* (2013.01)

(58) Field of Classification Search
CPC ............ A61F 2/2433; A61F 2002/9586; A61F 2230/0067; A61M 25/0013; A61M 25/0147; A61M 2025/0004
See application file for complete search history.

(56) References Cited

U.S. PATENT DOCUMENTS

| | | | | |
|---|---|---|---|---|
| 5,328,469 | A * | 7/1994 | Coletti | A61M 25/104 604/103.09 |
| 12,268,599 | B2 * | 4/2025 | Murad | A61F 2/958 |

(Continued)

FOREIGN PATENT DOCUMENTS

| | | |
|---|---|---|
| WO | WO 2022/046538 A | 3/2022 |

OTHER PUBLICATIONS

International Search Report and Written Opinion in International Appln. No. PCT/US2025/013753, mailed on May 16, 2025, 14 pages.

*Primary Examiner* — Suzette J Gherbi
(74) *Attorney, Agent, or Firm* — Fish & Richardson P.C.

(57) ABSTRACT

Delivery systems are used for medical devices. For example, this document describes delivery systems for implantable medical devices such as, but not limited to, prosthetic heart valves that are deliverable in a minimally invasive manner using a system of catheters. The delivery systems may include a valve stop member that establishes the longitudinal position of the prosthetic heart valve on a balloon member. Such a valve stop member can be constructed as a braided wire body or cellular body to provide multiple advantages.

48 Claims, 7 Drawing Sheets

(56) References Cited

U.S. PATENT DOCUMENTS

| | | | |
|---|---|---|---|
| 2009/0281619 A1* | 11/2009 | Le | A61M 25/01 623/2.11 |
| 2011/0130657 A1* | 6/2011 | Chomas | A61F 2/013 604/246 |
| 2011/0319988 A1* | 12/2011 | Schankereli | A61F 2/2418 623/2.11 |
| 2012/0022633 A1* | 1/2012 | Olson | A61F 2/2433 623/2.11 |
| 2012/0095550 A1* | 4/2012 | Gainor | A61F 2/2418 623/2.14 |
| 2015/0282931 A1* | 10/2015 | Brunnett | A61F 2/2466 623/2.37 |
| 2020/0352709 A1* | 11/2020 | Gurovich | A61F 2/2433 |
| 2023/0073466 A1 | 3/2023 | Anderson | |
| 2024/0390139 A1* | 11/2024 | Hummel | A61F 2/2418 |

\* cited by examiner

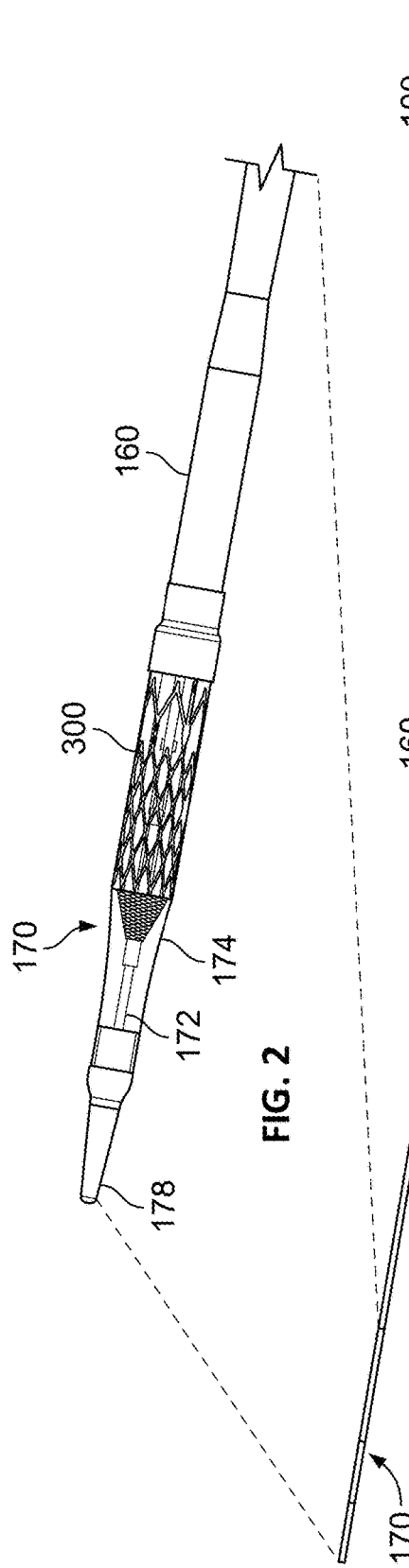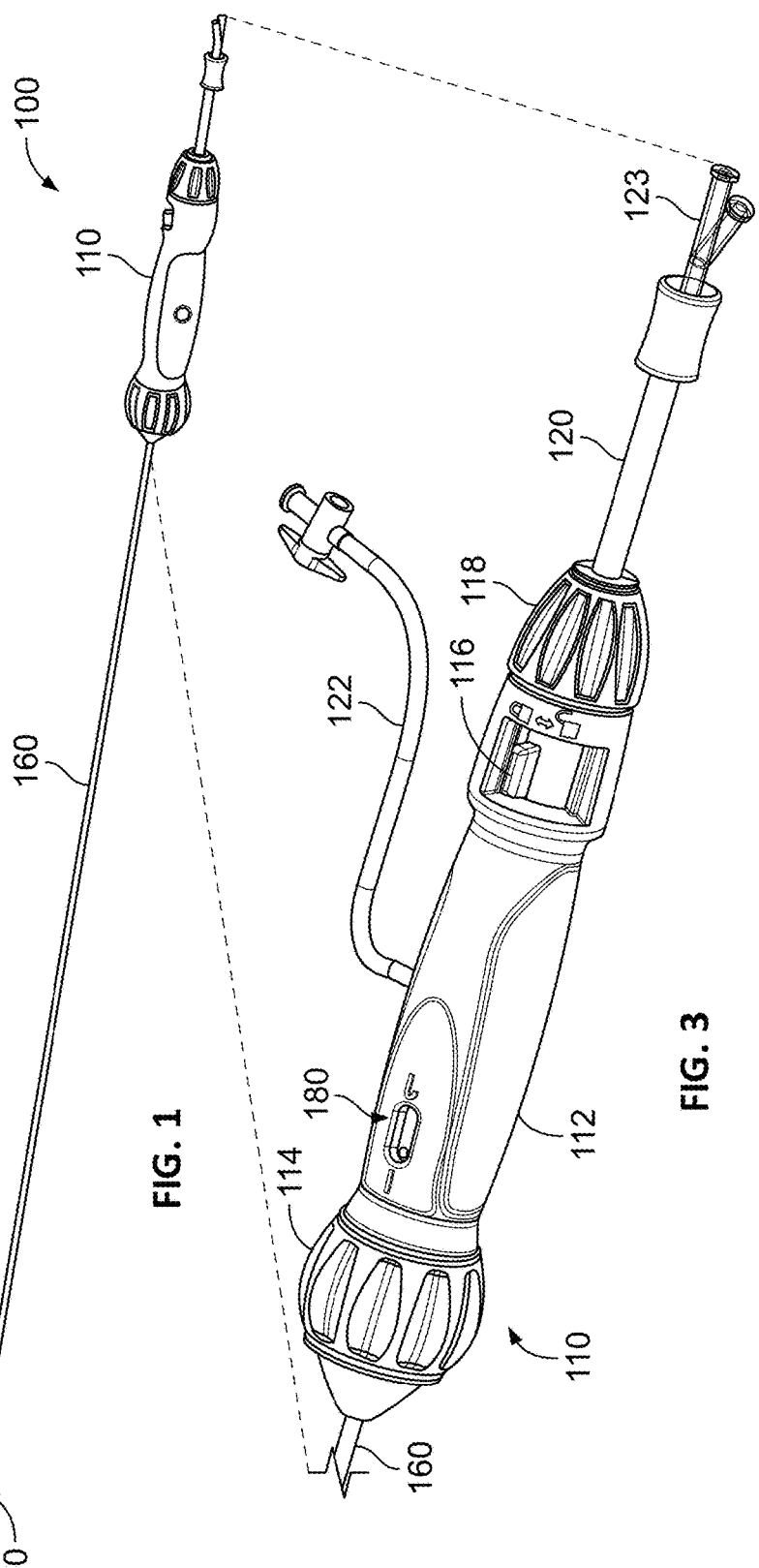

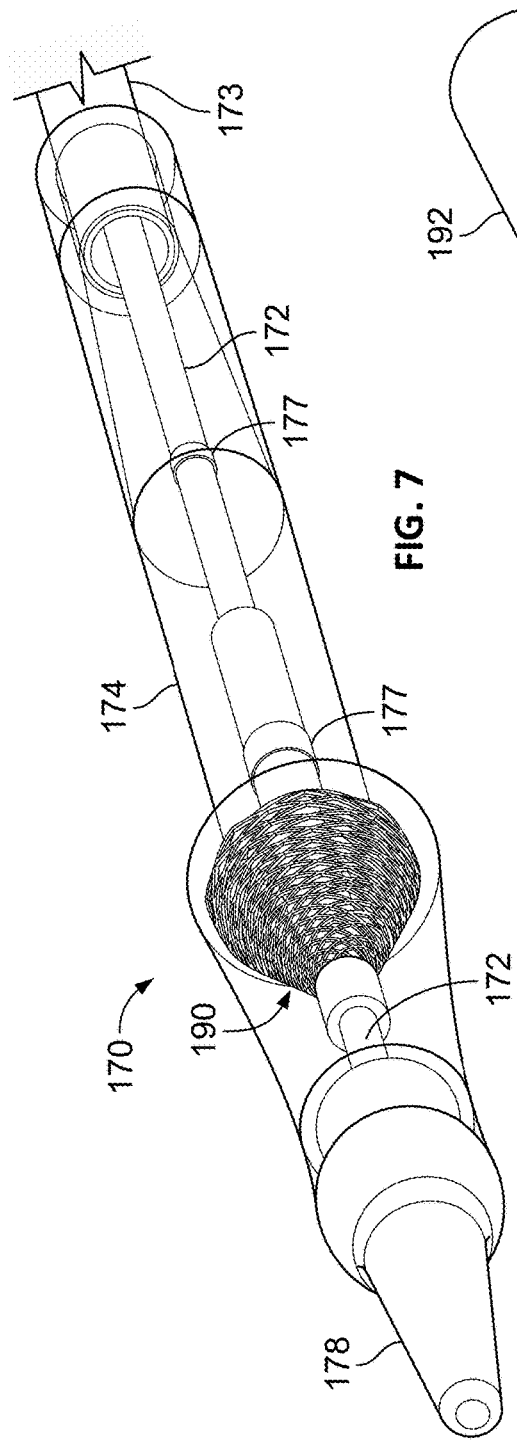
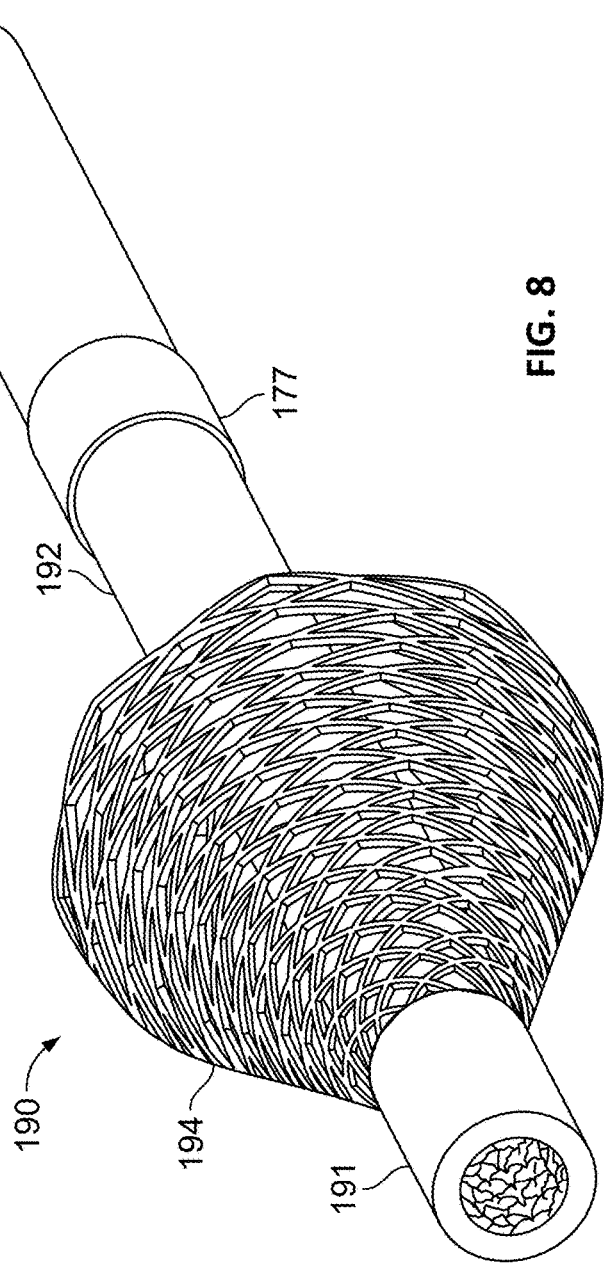
FIG. 7
FIG. 8

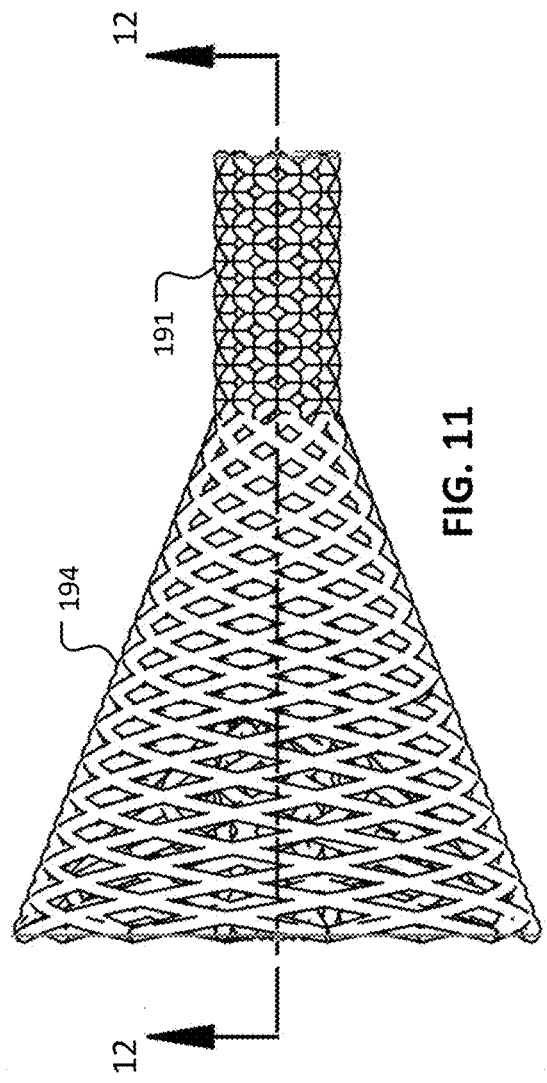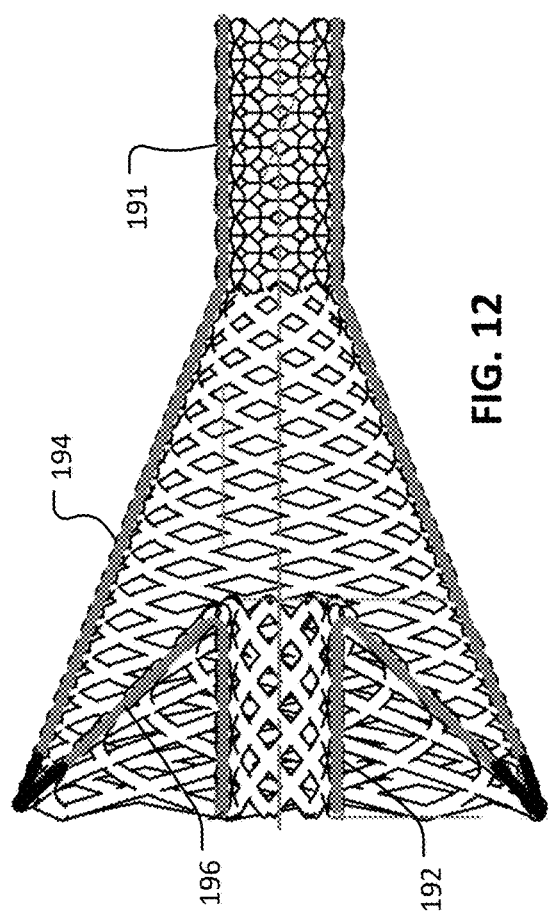
FIG. 11
FIG. 12

MEDICAL DEVICE DELIVERY SYSTEMS

CROSS-REFERENCE TO RELATED APPLICATIONS

This application claims the benefit of U.S. Provisional Application Ser. No. 63/554,666 filed Feb. 16, 2024. The disclosure of the prior application is considered part of (and is incorporated by reference in) the disclosure of this application.

BACKGROUND

1. Technical Field

This document relates to delivery systems for medical devices and methods for their use. For example, this document relates to delivery systems for implantable medical devices such as prosthetic heart valves that are deliverable in a minimally invasive manner using a system of catheters.

2. Background Information

Some prosthetic heart valves can be delivered in a minimally invasive fashion to avoid open-heart surgery. Such prosthetic heart valves can be delivered using a system of catheters that are manipulated by a clinician using an actuator handle and/or other types of control mechanisms that remain positioned external to the patient. For example, in some such cases, a prosthetic heart valve is compressed into a delivery catheter or sheath, which may be manually deflectable by adjusting a mechanism located on an actuator handle.

Transcatheter aortic valve replacement (TAVR) delivery systems can be used to deliver a prosthetic aortic valve to a native aortic heart valve site. Clinicians occasionally encounter difficulty when delivering prosthetic aortic valves in a minimally invasive manner using such catheter-based delivery systems. One such area of difficulty pertains to the task of navigating, in an atraumatic manner, the prosthetic aortic valve through the aortic arch pathway on the way to the native aortic heart valve location.

SUMMARY

This document describes delivery systems for medical devices and methods for their use. For example, this document describes delivery systems for implantable medical devices such as, but not limited to, prosthetic heart valves that are deliverable in a minimally invasive manner using a system of catheters. In some embodiments, the delivery systems include a valve stop member that establishes the longitudinal position of the prosthetic heart valve on a balloon member. Such a valve stop member can be constructed as a braided wire body or cellular body to provide multiple advantages, as described further herein.

In one aspect, this disclosure is directed to a medical device (e.g., prosthetic heart valve) delivery system that includes an elongate catheter comprising: (i) an outer catheter shaft and (ii) an inner catheter shaft extending distally beyond the outer catheter shaft; an inflatable balloon member attached at a distal end portion of the catheter; and a valve stop member attached to the inner catheter shaft and located within the balloon member. The valve stop member comprises a braided body or a cellular body.

Particular embodiments of the medical device delivery system may optionally include or more of the following features. The body of the valve stop member may comprise a frustoconical outer profile. The body of the valve stop member may further comprise an inverted frustoconical portion located within the frustoconical outer profile. The valve stop member may comprise the braided body, and the braided body may comprise a multi-element braided body. The multi-element braided body comprises at least 20 elements that are braided together. The valve stop member may comprise the cellular body, and the cellular body may comprise a laser-cut tube that is shape-set to have a frustoconical outer profile. The system may also include a nose cone attached to a distal end of the inner catheter shaft. In some embodiments, a distal end of the balloon member is attached to the nose cone. A proximal end of the balloon member may be attached to a distal end portion of the outer catheter shaft. The system may also include a steerable catheter defining a lumen and comprising a pull wire, wherein the catheter is slidably disposed within the lumen. A distal end portion of the valve stop member may be attached to the inner catheter shaft and a proximal end portion may be slidably coupled to the inner catheter shaft. A proximal end portion of the valve stop may comprise a polymeric tube that is slidably coupled to the inner catheter shaft.

In another aspect, this disclosure is directed to a method of assembling a prosthetic heart valve delivery system. The method can include: reducing an outer diameter of a valve stop member attached to an inner catheter shaft by longitudinally extending the valve stop member; passing a distal end portion of an inflatable balloon member over the valve stop member to position the valve stop member within the balloon member, wherein the outer diameter of the valve stop member expands after passing through the distal end portion of the balloon member; attaching the distal end portion of the balloon member to a nose cone that is attached to a distal end portion of the inner catheter shaft; and/or attaching a proximal end portion of the balloon member to an outer catheter shaft from which the inner catheter shaft distally extends.

Such a method of assembling a prosthetic heart valve delivery system may optionally include one or more of the following features. In some embodiments, the outer diameter of the valve stop member expands within the balloon member to a natural diameter that is greater than an inner diameter of the distal end portion of the balloon member. The valve stop member may comprise a braided body or a cellular body.

In another aspect, this disclosure is directed to a prosthetic heart valve delivery system. The system can include: an elongate catheter comprising: (i) an outer catheter shaft and (ii) an inner catheter shaft extending distally beyond the outer catheter shaft; an inflatable balloon member attached at a distal end portion of the catheter; and/or a valve stop member attached to the inner catheter shaft and located within the balloon member. The valve stop member defines an internal space within which a portion of the balloon member is located when a prosthetic heart valve is mounted on the balloon member in a position that is distally limited by the valve stop member.

Such a prosthetic heart valve delivery system may optionally include one or more of the following features. The valve stop member may comprise a braided body or a cellular body. In some embodiments, a body of the valve stop member comprises a frustoconical outer profile and an inverted frustoconical portion located within the frustoconical outer profile. The internal space may be defined within the inverted frustoconical portion.

In another aspect, this disclosure is directed to a prosthetic heart valve delivery system. The system includes an elongate catheter comprising: (i) an outer catheter shaft and (ii) an inner catheter shaft extending distally beyond the outer catheter shaft; an inflatable balloon member attached at a distal end portion of the catheter shaft, the balloon member having a distal opening with an inner diameter prior to being attached to the distal end portion of the catheter shaft; and a valve stop member attached to the inner catheter shaft and located within the balloon member. The valve stop member has an outer diameter that is adjustable between a contracted diameter that is less than the inner diameter and a natural diameter that is greater than the inner diameter.

Such a prosthetic heart valve delivery system may optionally include one or more of the following features. The valve stop member may comprise a braided body or a cellular body. The natural diameter may be adjustable to the contracted diameter by longitudinally stretching the braided body or the cellular body.

Particular embodiments of the subject matter described in this document can be implemented to realize one or more of the following advantages.

In some embodiments, the valve stop member is located within the balloon member and the braided or cellular structure of the valve stop member allows for a desired expansion process of the balloon member because the flow of the inflation medium is substantially uninhibited by the valve stop member.

In some embodiments, the flexibility of the braided or cellular structure of the valve stop member allows for tracking of valve stop member and prosthetic heart valve along a curved pathway in an advantageous manner. That is, internal portions of the valve stop member can flex while tracking along the curved pathway while other portions of the valve stop member against which the prosthetic heart valve is pressed do not substantially deform. Said another way, portions of the valve stop member can flex or extend while tracking along a curved path while a proximal section of the nose cone does not move relative to the crimped valve on the balloon member. Accordingly, a distal end of the prosthetic heart valve can remain reliably compressed against the valve stop member to provide positional control and to protect the blood vessel walls of the patient by keeping the distal end of the prosthetic heart valve concealed by the valve stop member during advancement.

In some embodiments, the braided or cellular structure of the valve stop member allows for an advantageous assembly process of the prosthetic heart valve delivery systems described herein. For example, the natural outer diameter of the braided or cellular structure of the valve stop member can be reduced by longitudinally stretching the valve stop member. The reduced outer diameter of the valve stop member allows the valve stop member to be placed within a balloon member that has an end opening that is smaller than the natural outer diameter of the valve stop member.

In some embodiments, the valve stop member defines an internal space within which a portion of the balloon member extend so that the prosthetic heart valve on the balloon member can be longitudinally located on the balloon member in a consistent and predictable manner.

In some embodiments, the valve stop member has a high level of radial compressive strength that, in some embodiments, can be advantageously used to radially expand a delivery sheath. Moreover, the valve stop member can also have a high level of longitudinal compressive strength that can be advantageously used to maintain the longitudinal position of the prosthetic heart valve on the balloon member.

The longitudinal force of the valve stop enables the steerable shaft of the delivery system to be loaded under compressive forces, which also aids in the tracking mentioned above.

In some embodiments, the medical device delivery systems described herein are advantageously designed to enable rotary adjustments of the balloon catheter on which the prosthetic heart valve is mounted in order to facilitate a desired alignment the of prosthetic valve's structure with the commissures of the native heart valve. In some embodiments, a steerable catheter is included as part of the medical device delivery systems described herein, and such a steerable catheter can be controllably deflected by 180° or more. Such deflection is advantageous while navigating the catheters within the patient including, navigation of the aortic arch, for example. In some such embodiments, a deflection indicator is included on the control handle of the medical device delivery systems described herein. Such an indicator is advantageous to clinicians by providing a readily available indication of the amount of deflection of the catheters that are within the patient. In some embodiments, a locking mechanism is included on the control handle of the medical device delivery systems described herein. Such a locking mechanism can be activated to advantageously lock together (longitudinally) the catheters of the medical device delivery systems during the advancement and retraction steps of the medical device deployment process. Moreover, the locking mechanism can be unlocked to allow for relative movements of the catheters, as described herein.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 1 is a perspective view of an example medical device delivery system in accordance with some embodiments provided herein.

FIG. 2 is an enlarged perspective view of an example distal end portion of the medical device delivery system of FIG. 1.

FIG. 3 is an enlarged perspective view of an example handle of the medical device delivery system of FIG. 1.

FIG. 7 is a perspective view of the distal end portion of the medical device delivery system of FIG. 1 without the implantable medical device.

FIG. 8 is a perspective view of an example valve stop member in accordance with some embodiments.

FIG. 11 is a plan view of the braided body of the valve stop member of FIG. 8.

FIG. 12 is a cross-sectional view of the valve stop member of FIG. 11.

Like reference numbers represent corresponding parts throughout.

DETAILED DESCRIPTION

Figure 4:
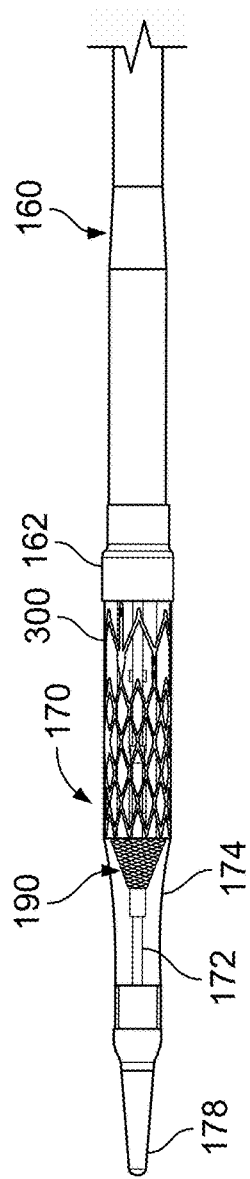
FIG. 4 is a plan view of the distal end portion of the medical device delivery system of FIG. 1 in a delivery configuration.

This document describes delivery systems for medical devices and methods for their use. For example, this document describes delivery systems for implantable medical devices such as, but not limited to, prosthetic heart valves that are deliverable in a minimally invasive manner using a system of catheters. In some embodiments, the delivery systems include a valve stop member that establishes the longitudinal position of the prosthetic heart valve on a balloon member. Such a valve stop member can be constructed as a braided wire body or cellular body to provide multiple advantages, as described further herein.

FIG. 1 illustrates an example transcatheter medical device delivery system 100. In the depicted example, the medical device delivery system 100 is configured to deliver a prosthetic heart valve to a native heart valve location by advancing the prosthetic heart valve to the heart via the vascular system of the patient. For example, in some embodiments the medical device delivery system 100 can be used to deliver a prosthetic aortic valve to a site of a native aortic valve via the aorta of the patient. This non-limiting type of use of the medical device delivery system 100 is used as an example herein to describe the functionality of the medical device delivery system 100. In such a case, the medical device delivery system 100 may be inserted into a femoral artery via a sheath and then advanced to the aorta, through the aortic arch, and to the native aortic valve site. Alternative approaches, such as trans-subclavian, trans-carotid, trans-radial, and others are also envisioned using the medical device delivery system 100.

Broadly speaking, the medical device delivery system 100 includes a clinician control handle 110 (or simply "handle 110"), a steerable catheter 160, and an elongate catheter 170 (referred to hereinafter as a balloon catheter 170). The steerable catheter 160 and the balloon catheter 170 each extend distally from the handle 110. The steerable catheter 160 and the balloon catheter 170 are each affixed to the handle 110, but at different locations of the handle 110 (as described further below).

FIG. 2 shows an expanded view of a distal end portion of the steerable catheter 160 and the balloon catheter 170. An example prosthetic heart valve 300 is mounted on the balloon catheter 170 in a low-profile delivery configuration.

The steerable catheter 160 defines a lumen in which the balloon catheter 170 is slidably disposed. That is, the balloon catheter 170 can be manipulated by the clinician (using the handle 110) to advance and/or retract the balloon catheter 170 (and the prosthetic heart valve 300) relative to the steerable catheter 160 by sliding the balloon catheter 170 within the lumen of the steerable catheter 160. For example, in some cases the steerable catheter 160 can be proximally pulled back relative to the balloon catheter 170 and the prosthetic heart valve 300, as described further below. The steerable catheter 160 is controllably deflectable or steerable by the clinician (using the handle 110 to manipulate a pull wire, as described further below in reference to FIG. 3). In particular, a distal end portion of the steerable catheter 160 is controllably deflectable to any desired angle up to approximately 180°, or even more than 180° in some embodiments. When the steerable catheter 160 is deflected in that manner, the balloon catheter 170 also takes on the same extent of deflection (because the balloon catheter 170 is positioned within the lumen of the steerable catheter 160). The deflection of the steerable catheter 160 (and the balloon catheter 170) can be useful for navigating the aortic arch, for example. In some embodiments, the balloon catheter 170 (and the steerable catheter 160) can be advanced over a pre-placed guidewire.

Still referring to FIG. 2, the balloon catheter 170 includes an inner catheter shaft 172 and a balloon 174 mounted on a distal end portion of the balloon catheter 170. The catheter shaft 172 defines an inflation lumen and one or more openings (not visible) through which an inflation fluid can be supplied and withdrawn in order to controllably inflate and/or deflate the balloon 174. In addition, the inner catheter shaft 172 defines a central lumen by which the balloon catheter 170 (and the steerable catheter 160) can be advanced over a guidewire.

In the depicted embodiment, a tapered nose cone 178 is attached to a distal end of the inner catheter shaft 172 and to the balloon 174. The nose cone 178 extends distally from the balloon 174 and provides an atraumatic leading distal end of the medical device delivery system 100.

The prosthetic heart valve 300 can be crimped on the balloon 174 in a radially compressed, low-profile delivery configuration. Then, as described further below, when the balloon 174 and the prosthetic heart valve 300 are positioned at a target location and in a desired orientation relative to the patient's anatomy, the balloon 174 can be inflated to radially expand the prosthetic heart valve into engagement with the native anatomy of the patient (e.g., into engagement with the annulus of a native heart valve such as the native aortic valve). Thereafter, the balloon 174 can be deflated and retracted from the prosthetic heart valve 300. In some embodiments, radiopaque markers can be located on one or more locations of the steerable catheter 160 and/or the balloon catheter 170 to provide visualization of the steerable catheter 160 and/or the balloon catheter 170 under fluoroscopy.

FIG. 3 shows an enlarged view of an example handle 110 of the medical device delivery system 100. The handle 110 remains external to the patient while the steerable catheter 160, the balloon catheter 170, and the prosthetic heart valve 300 extend internally to the patient (e.g., into the vasculature and/or heart of the patient). The handle 110 includes multiple control mechanisms by which a clinician operator can remotely manipulate various aspects of the steerable catheter 160 and the balloon catheter 170, as described further below. The steerable catheter 160 is fixed to the handle 110.

In this view of the handle 110, the following components and/or control mechanisms of the handle 110 are in view. That is, the handle 110 includes a housing 112, a rotatable first actuator knob 114, a locking actuator 116, a rotatable second actuator knob 118, a balloon catheter pull rod 120, a flush line 122, and an optional deflection indicator 180.

The first actuator knob 114, the second actuator knob 118, and the locking actuator 116 are each manually rotatable relative to the housing 112. The steerable catheter 160 can be laterally deflected by rotation of the first actuator knob 114. That is, manual rotations of the first actuator knob 114 can be used to control the extent of deflection of the steerable catheter 160 (and the balloon catheter 170 disposed therein) by tensioning or relaxing a pull wire (not shown). The deflection indicator 180 can provide an indication of the extent of deflection of the steerable catheter 160. The second actuator knob 118 can be rotated to rotate the balloon catheter 170 (and the prosthetic heart valve 300) relative to the steerable catheter 160.

A proximal end of the balloon catheter 170 is affixed to the balloon catheter pull rod 120. The balloon catheter pull rod 120 is manually translatable relative to the housing 112 (when the locking actuator 116 is in its unlocked position). The balloon catheter pull rod 120 can be extended and retracted relative to the housing 112 to extend and retract the balloon catheter 170 (and the prosthetic heart valve 300) relative to the steerable catheter 160. The locking actuator 116 can be used to lock and unlock the movability of the balloon catheter pull rod 120 relative to the housing 112.

FIG. 4 provides another view of the distal end portion of the medical device delivery system 100, including the steerable catheter 160 and the balloon catheter 170. The prosthetic heart valve 300 is mounted on the balloon 174 of the balloon catheter 170. The nose cone 178 and the inner catheter shaft 172 of the balloon catheter 170 are also visible. The depicted configuration is the delivery configuration that is used when advancing the distal end portion of the medical device delivery system 100 and the prosthetic heart valve 300 to a target location for deployment of the prosthetic heart valve 300 within a patient (e.g., to a native heart valve region).

In addition, a valve stop member 190 is shown. The valve stop member 190 is attached to the inner catheter shaft 172 and located within the balloon 174. Additional features of the valve stop member 190 are described below.

In the depicted delivery configuration, the prosthetic heart valve 300 is longitudinally compressed and securely captured between a flared distal end 162 of the steerable catheter 160 and the valve stop member 190. The flared distal end 162 defines an annular space that receives and covers an end portion of the prosthetic heart valve 300. That is, an end portion of the prosthetic heart valve 300 (e.g., of the metallic stent frame of the prosthetic heart valve 300) is concealed by the flared distal end 162 of the steerable catheter 160. This arrangement helps to prevent the potential for vessel wall damage that the end portion of the prosthetic heart valve 300 may otherwise incur if the end portion was exposed (rather than being concealed by the flared distal end 162 of the steerable catheter 160). Accordingly, during transvascular advancement of the depicted arrangement, the coverage of the end portion of the prosthetic heart valve 300 by the flared distal end 162 mitigates risks of vessel wall damage that could result if that end portion was to make contact with the vessel walls.

The other end of the prosthetic heart valve 300 is held in position by the valve stop member 190. The valve stop member 190 prevents the prosthetic heart valve 300 from moving distally despite the longitudinal force from the flared distal end 162 of the steerable catheter 160 that would otherwise engender such distal movement. Accordingly, the prosthetic heart valve 300 is captured between the steerable catheter 160 and the valve stop member 190.

More specifically, because the valve stop member 190 resides within the balloon 174, a layer of the flexible wall material of the balloon 174 resides between the prosthetic heart valve 300 and the valve stop member 190. That flexible wall material of the balloon 174 is compressed between the prosthetic heart valve 300 and the valve stop member 190 in the depicted delivery configuration.

Figure 5:
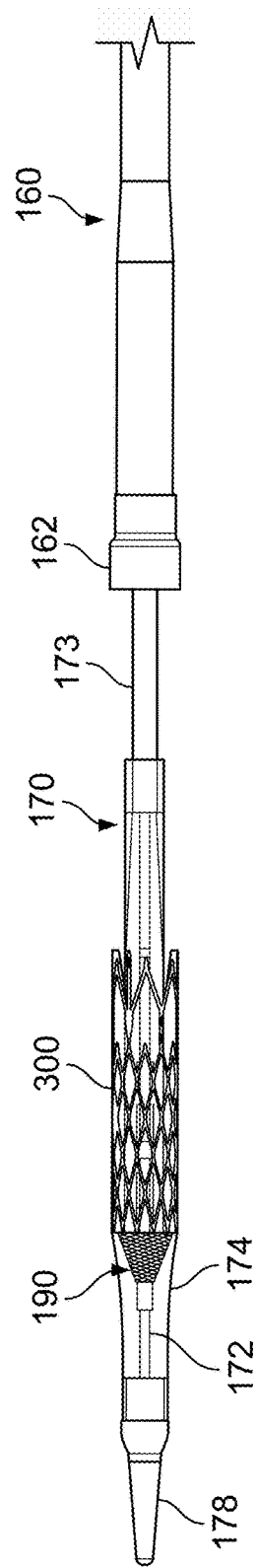
FIG. 5 is a plan view of the distal end portion of the medical device delivery system of FIG. 1 in an intermediate configuration.

FIG. 5 depicts a latter stage of the delivery/deployment process of the prosthetic heart valve 300 using the medical device delivery system 100. In comparison to the arrangement of FIG. 4, here the steerable catheter 160 has been pulled proximally back in relation to the balloon catheter 170, and in relation to the prosthetic heart valve 300 that is mounted on the balloon 174 of the balloon catheter 170.

The depicted arrangement reveals that the balloon catheter 170 also includes an outer catheter shaft 173. The inner catheter shaft 172 extends distally from the outer catheter shaft 173. The proximal end of the balloon 174 is attached to a distal end portion of the outer catheter shaft 173. The distal end of the balloon 174 is attached to the tapered nose cone 178, which is attached to a distal end portion of the inner catheter shaft 172. The valve stop member 190 is within the balloon 174 and longitudinally positioned between the outer catheter shaft 173 and the tapered nose cone 178. The valve stop member 190 is close to the tapered nose cone 178 than to the distal end of the outer catheter shaft 173.

Figure 6:
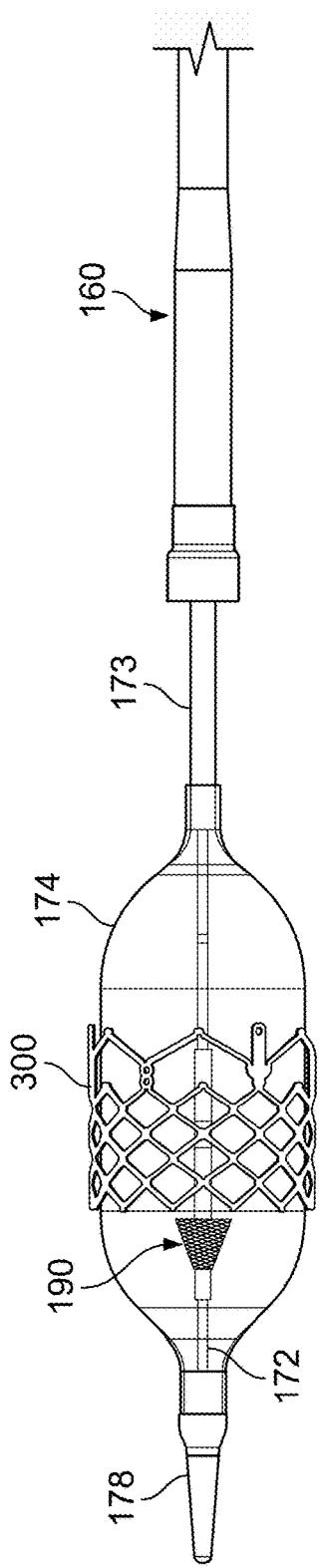
FIG. 6 is a plan view of the distal end portion of the medical device delivery system of FIG. 1 in an expanded configuration.

FIG. 6 depicts yet another latter stage of the delivery/deployment process of the prosthetic heart valve 300 using the medical device delivery system 100. In this arrangement, the balloon 174 has been inflated and the prosthetic heart valve 300 has been radially expanded as a result. This expansion of the prosthetic heart valve 300 may be performed, for example, once the prosthetic heart valve 300 has been longitudinally and/or rotationally positioned properly in relation to a native heart valve annulus. That is, the unexpanded prosthetic heart valve 300 can be properly positioned in relation to the native anatomy, and then the prosthetic heart valve 300 can be expanded by inflation of the balloon 174.

FIG. 7 illustrates a distal end portion of the balloon catheter 170. As shown, the balloon catheter 170 includes the inner catheter shaft 172, the outer catheter shaft 173, the balloon 174, the tapered nose cone 178, and the valve stop member 190. Radiopaque markers 177 may be located on various positions of the inner catheter shaft 172 and the valve stop member 190.

Figure 9:
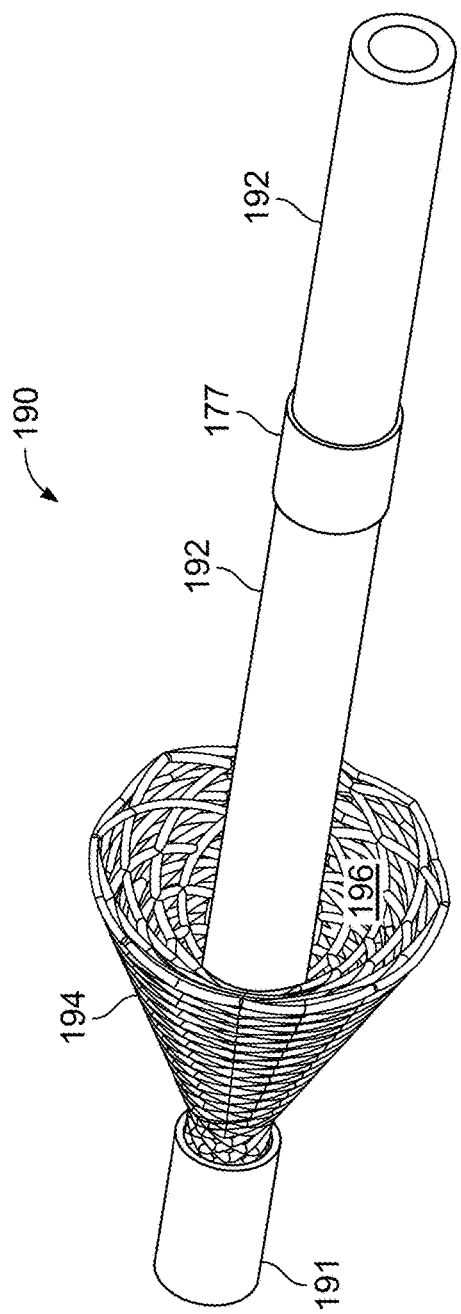
FIG. 9 is another perspective view of the valve stop member of FIG. 8.

FIGS. 8 and 9 show the valve stop member 190 in isolation so that additional details of its construction are visible. The valve stop member 190 includes a distal hub 191, an elongate proximal hub 192, a frustoconical outer surface 194, and an inner inverted frustoconical surface 196.

The distal hub 191 is attached/affixed to the inner catheter shaft 172 such that it is held in a constant position. The elongate proximal hub 192, however, is a polymeric or metallic tube that is slidable along the inner catheter shaft 172 rather than being attached to the inner catheter shaft 172. More particularly, the elongate proximal hub 192 comprises an elongate tube that defines a lumen in which the inner catheter shaft 172 is slidably disposed. The elongate proximal hub 192 can slide along the inner catheter shaft 172. As described further below, during the assembly of the balloon catheter 170 the elongate proximal hub 192 is forcibly slid along the inner catheter shaft 172 to longitudinally stretch the valve stop member 190 and to thereby reduce the outer diameter of the frustoconical outer surface 194 so that the balloon 174 can be moved into position over the valve stop member 190.

Figure 10:
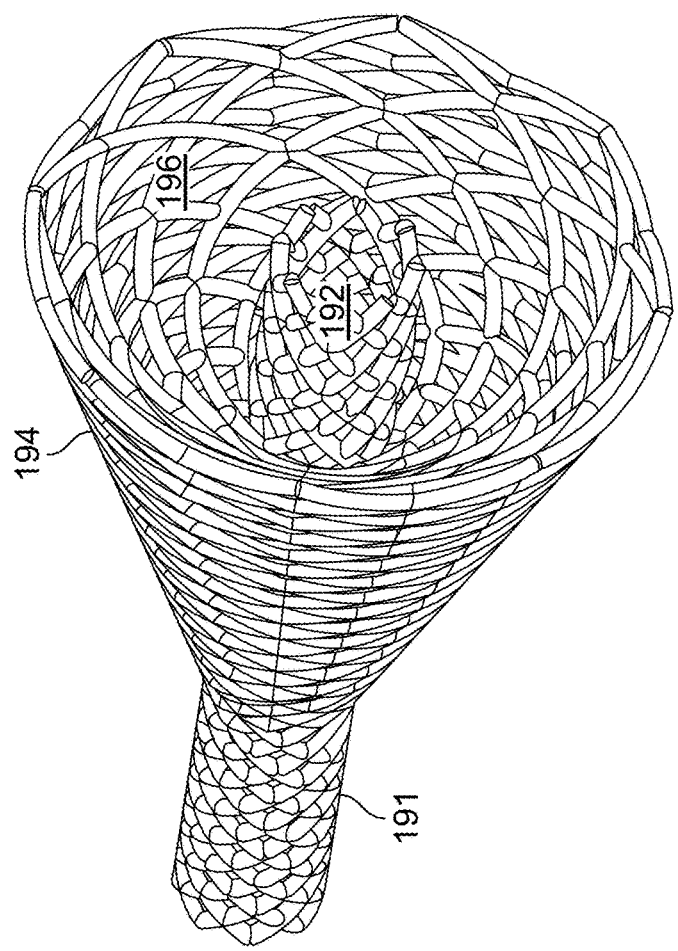
FIG. 10 is a perspective view of the braided body of the valve stop member of FIG. 8.

Referring also to FIGS. 10-12, the main body of the valve stop member 190 is made of an open structure that can be constructed in various ways such as, but not limited to, a braided wire structure, a laser-cut tube and expanded stent-like structure, and the like. In some embodiments, the structure can be heat-set in the depicted configuration so that the depicted configuration is the natural shape. Accordingly, if/when the shape is deformed for any reason it will rebound to the depicted natural shape when released from external forces.

In some embodiments, the main body of the valve stop member 190 (e.g., as depicted in FIGS. 10-12) is a braided wire structure that is made of one or more wires, or multiple wires that are braided together. In other words, in some embodiments the main body of the valve stop member 190 may be a multi-element braided body. Such wires/elements may be made of various materials such as, but not limited to, nitinol (nickel titanium), stainless steel, other metal alloys, polymeric materials, and the like, and combinations thereof.

In some embodiments, the braided wire structure of the main body of the valve stop member 190 includes a single wire, or from one to ten wires, or from ten to twenty wires, or from twenty to thirty wires, or from thirty to forty wires, or more than forty wires. In some embodiments, the braided wire structure of the main body of the valve stop member 190 includes at least ten wires, or at least twenty wires, or at least thirty wires, or at least forty wires.

As best seen in FIG. 12, the main body of the valve stop member 190 defines or includes the inverted frustoconical surface 196. The inverted frustoconical surface 196 is radially within the frustoconical outer surface 194. The open frustoconical space defined between the inverted frustoconical surface 196 and the elongate proximal hub 192 provides room for some of the flexible wall material of the balloon 174 to reside. That is, when the prosthetic heart valve 300 is captured between the steerable catheter 160 and the valve stop member 190 (e.g., as shown in FIG. 4), some of the flexible wall material of the balloon 174 extends into the open frustoconical space defined between the inverted frustoconical surface 196 and the elongate proximal hub 192. This is an advantageous arrangement because the prosthetic heart valve 300 can thereby abut against the valve stop member 190 (with two layers of the flexible wall material of the balloon 174 therebetween) in an orderly and predictable manner. In other words, the end of the prosthetic heart valve 300 will be predictably positioned away from the valve stop member 190 by a distance equal to the thickness of two layers of the flexible wall material of the balloon 174. In some embodiments, the proximal edge of the elongate proximal hub 192 is within the open frustoconical space defined between the inverted frustoconical surface 196 and the elongate proximal hub 192. This can allow for the frame of the prosthetic heart valve 300 to be crimped as radially small as possible and in a predictable manner.

The shape and open construction of the main body of the valve stop member 190 also provide advantages while the assembly is being advanced/tracked along a curved path (e.g., along the aortic arch). More specifically, the shape and wire construct of the inverted frustoconical surface 196 acts like a deflectable suspension while the assembly is being tracked along curved paths. Accordingly, the full circumference of the prosthetic heart valve 300 can remain reliably abutted against the valve stop member 190 (with two layers of the flexible wall material of the balloon 174 therebetween) as the assembly is being tracked along curved paths. This keeps the assembly in an atraumatic arrangement because no pointed edges of the prosthetic heart valve 300 that could injure a vessel wall become exposed as it travels along a curvature. Instead, the bending/flexure of the main body of the valve stop member 190 is performed by the inverted frustoconical surface 196.

In some embodiments, the shape and open construction of the main body of the valve stop member 190 also provide advantages during manufacturing of the balloon catheter 170. In particular, the main body of the valve stop member 190 can be longitudinally stretched to cause a reduction in the maximum natural outer diameter of the frustoconical outer surface 194. That reduction in the outer diameter of the frustoconical outer surface 194 can allow the valve stop member 190 to pass through an opening of the balloon 174 that is smaller than the natural maximum outer diameter of the frustoconical outer surface 194. Once the valve stop member 190 has been placed within the balloon 174, then the main body of the valve stop member 190 will self-rebound to its natural configuration (as shown) in which the maximum outer diameter of the frustoconical outer surface 194 is larger than the opening of the balloon 174 it was passed through.

Figure 13:
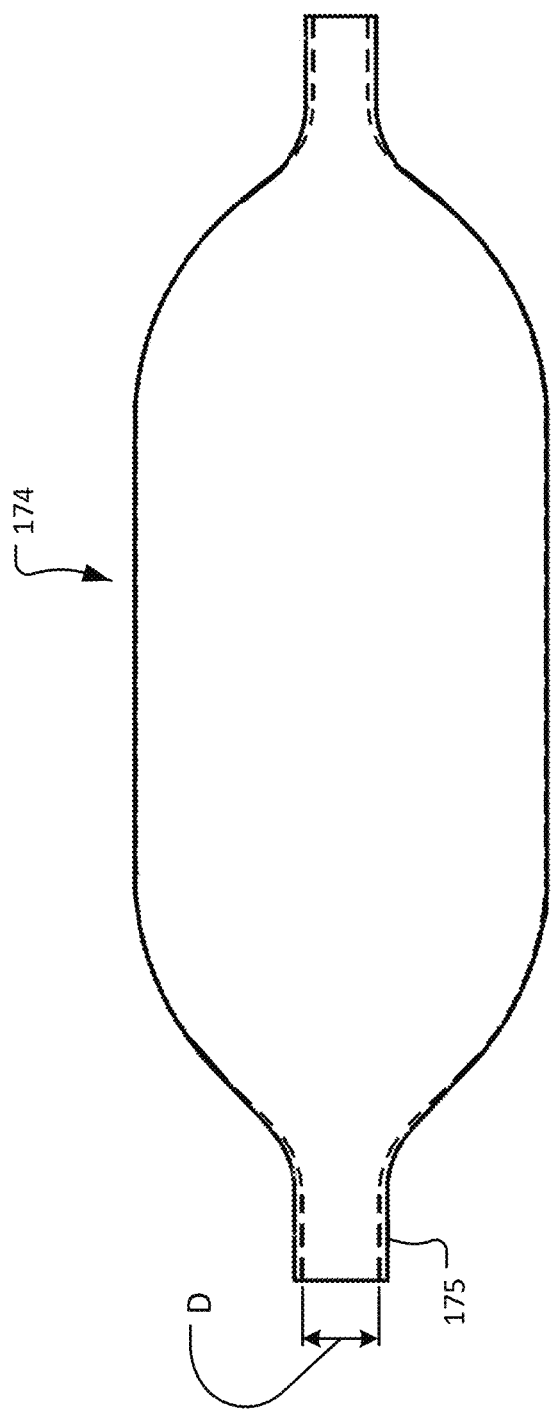
FIG. 13 is a plan view of an example balloon member of the medical device delivery systems in accordance with some embodiments.

FIG. 13 shows the balloon 174 in its expanded configuration. The distal end 175 of the balloon 174 that gets attached to the tapered nose cone 178 (e.g., see FIGS. 4-7) has an opening with an inner diameter D. The diameter D is smaller than the natural maximum outer diameter of the frustoconical outer surface 194. However, when the main body of the valve stop member 190 is stretched, the maximum outer diameter of the frustoconical outer surface 194 can be made smaller than the diameter D. Accordingly, the valve stop member 190 can be placed inside of the balloon 174 by passing it through the opening of the distal end 175 of the balloon 174 while the main body of the valve stop member 190 is maintained in a stretched condition. After the placement of the valve stop member 190 inside of the balloon 174 and the relieving of the tension, the main body of the valve stop member 190 will relax and rebound to its natural configuration (as shown in FIGS. 4-12) in which the maximum outer diameter of the frustoconical outer surface 194 is larger than the diameter D of the distal end 175 of the balloon 174.

Figure 14:
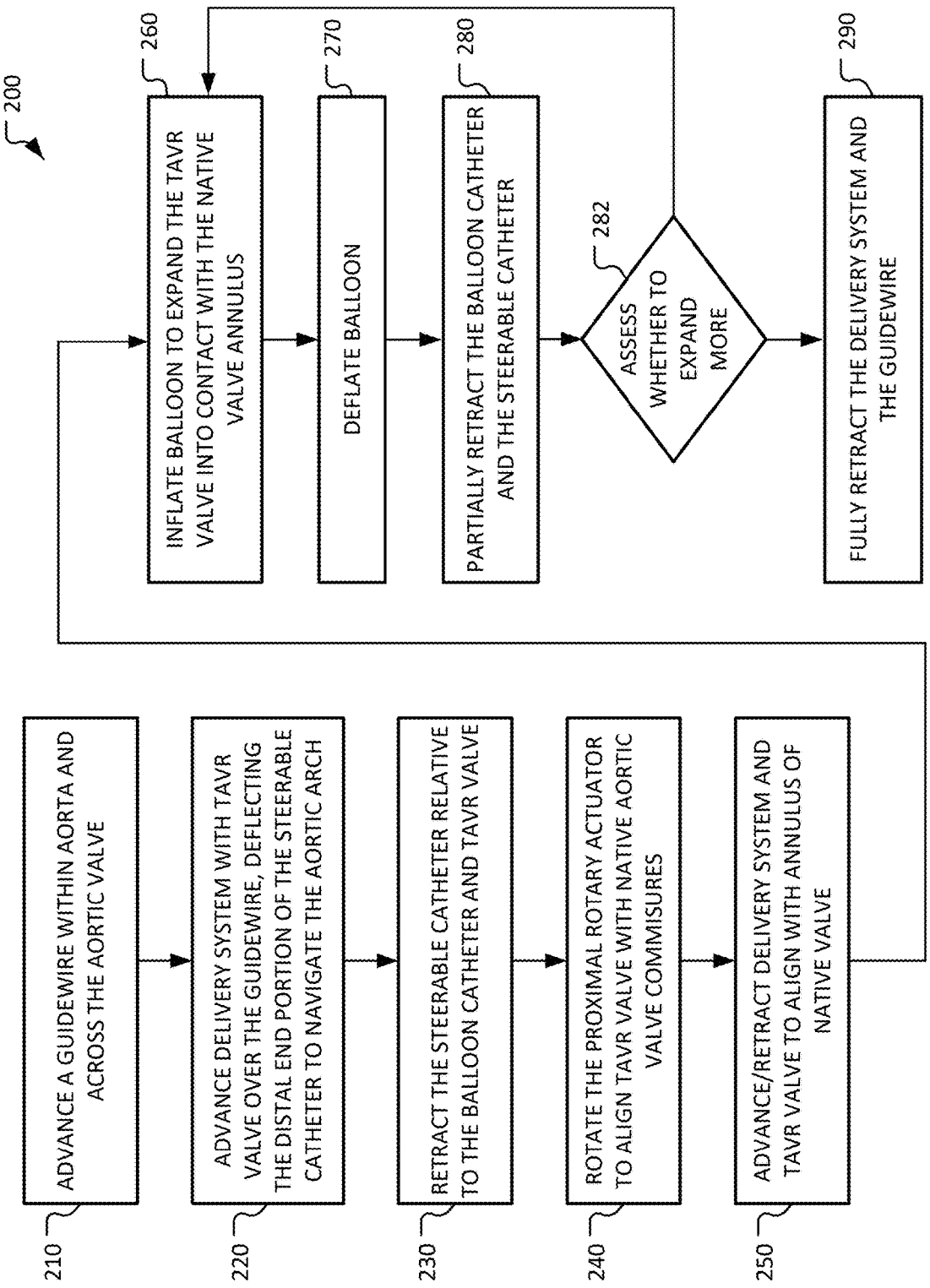
FIG. 14 is a flowchart of an example method for the delivery of a medical device using the delivery systems described herein.

FIG. 14 is a flowchart of an example method 200 for the delivery and deployment of a medical device using the medical device delivery system 100. In particular, the example method 200 is for delivering a prosthetic aortic valve (e.g., the prosthetic heart valve 300) using the medical device delivery system 100. Each step of the method 200 will be explained, and references will be made to other figures to describe how a clinician can manipulate the medical device delivery system 100 to perform the steps of the method 200.

This method 200 can be performed by a clinician while using fluoroscopic imaging (and/or other types of imaging) in some cases. In addition, other conventional steps for preparing the medical device delivery system 100 (e.g., flushing, testing, etc.) may be performed prior to the first step 210, but are not specifically included in the flowchart of FIG. 14.

At the first step 210 of the method 200, a guidewire is inserted into the patient. For example, in some embodiments the guidewire is inserted into a femoral artery and then navigated into the aorta, over the aortic arch, and across the aortic valve. A distal end portion of the guidewire is located in the left ventricle of the patient.

At step 220, with the locking actuator 116 (FIG. 3) in the locked position, the medical device delivery system 100 (with a prosthetic aortic valve 300 mounted in a radially compressed configuration on the balloon 174) is advanced over the guidewire. As the balloon catheter 170 and steerable catheter 160 are advanced over the aortic arch, the clinician can deflect the steerable catheter 160 (and the balloon catheter 170 contained therein) accordingly. That is, the clinician can rotate the first actuator knob 114 relative to the housing 112 to add tension to the pull wire, resulting in deflection of the steerable catheter 160 (and the balloon catheter 170 contained therein) to help navigate the aortic arch. The advancement of step 220 can continue until the prosthetic aortic valve 300 is positioned generally within the native aortic valve.

At step 230, with the prosthetic aortic valve 300 remaining positioned generally within the native aortic valve, the clinician can move the locking actuator 116 (FIG. 3) to its unlocked position and then pull the housing 112 proximally while holding the balloon catheter pull rod 120 in a generally stationary position. These actions will pull back the steerable catheter 160 relative to the balloon catheter 170 (and the prosthetic heart valve 300 mounted thereon) as shown in FIG. 5. The balloon catheter pull rod 120 will be extended into the housing 112 as a result.

Next, at step 240 and with the locking actuator 116 relocked, the clinician can rotate the balloon catheter 170 (and the prosthetic heart valve 300 mounted thereon) to align structural features of the prosthetic heart valve 300 relative to anatomical features of the native aortic valve. The clinician can perform this step by rotating the second actuator knob 118 relative to the housing 112. The balloon catheter 170 will rotate in response to the rotations of second actuator knob 118, but the steerable catheter 160 will remain stationary. The clinician can use fluoroscopic imaging to observe radiopaque markers on the prosthetic heart valve 300 to align the prosthetic heart valve 300 in a desired orientation relative to the native heart valve anatomy (e.g., relative to commissures of the native heart valve). With the desired orientation attained, the clinician can then manipulate the locking actuator 116 to its locked position.

At step 250 and with the locking actuator 116 in its locked position, the clinician can then advance or retract the medical device delivery system 100 (with the prosthetic heart valve 300 still mounted on the balloon 174 of the balloon catheter 170) to position the prosthetic heart valve 300 in a desired longitudinal position relative to the annulus of the native aortic valve. In some embodiments, the prosthetic heart valve 300 can include a radiopaque marker that indicates where the prosthetic heart valve 300 should be longitudinally located relative to the annulus of the native aortic valve. The clinician can simply push the handle 110 distally or pull the handle 110 proximally to perform this step.

At step 260 and with the locking actuator 116 still in its locked position, the clinician can then initiate rapid pacing and when in optimal position, inflate the balloon 174 to expand the prosthetic heart valve 300 into contact with the annulus of the native aortic valve, as depicted in FIG. 6. For example, the clinician can inject an inflation liquid (e.g., saline, a mixture of saline and a contrast media, etc.) into the inflation lumen of the balloon catheter 170 via a port 123 (FIG. 3) extending from the balloon catheter pull rod 120 to inflate the balloon 174 (and expand the prosthetic heart valve 300).

At step 270 and with the locking actuator 116 still in its locked position, the clinician can then deflate the balloon 174 (to uncouple the balloon 174 from the prosthetic heart valve 300 which remains engaged with the annulus of the native aortic heart valve). To deflate the balloon 174, the clinician can withdraw the inflation liquid from the balloon 174 by performing the reverse of the injection step. After the deflation of the balloon 174 the pacing is ceased. In some cases, the clinician can then manipulate the locking actuator 116 to its unlocked position.

At step 280, the clinician can retract the balloon catheter 170 and the steerable catheter 160 away from the prosthetic heart valve 300 (which remains engaged with the annulus of the native aortic heart valve) by pulling them proximally. The balloon 174 is proximally retracted at least far enough to allow the prosthetic heart valve 300 to begin to function. This can be performed by simultaneously pulling both the balloon catheter 170 and the steerable catheter 160 proximally, or by pulling the balloon catheter 170 proximally relative to the steerable catheter 160. The balloon 174 is thereby removed from being within the prosthetic heart valve 300 and the prosthetic heart valve 300 will begin to function.

At step 282, an assessment can be made by the clinician (or clinical team) to determine whether the prosthetic heart valve 300 should be expanded further. To make this assessment, the clinician can consider various factors. The factors that may be considered by the clinician can include, for example, the extent of calcification of the native valve annulus, the extent (if any) of paravalvular leakage (e.g., as visualized/indicated using Doppler ultrasound imaging), one or more fluoroscopic images of the prosthetic heart valve 300 relative to the anatomy, and the like. In some cases, one or more mathematical calculations may also be made to assist with the decision process.

If the assessment at step 282 indicates that additional expansion of the prosthetic heart valve 300 is desirable, the method 200 can return to step 260 for additional expansion of the balloon 174 and the prosthetic heart valve 300. For example, in some cases an additional injection of ½ ml to 1 ml of inflation liquid (e.g., saline) beyond the originally injected amount can be delivered to cause a relatively small additional expansion of the balloon 174 and the prosthetic heart valve 300. Thereafter, the method 200 can once again proceed to step 270 and so on.

If the assessment at step 282 indicates that no additional expansion of the prosthetic heart valve 300 is desirable, the method 200 can proceed to step 290.

In some embodiments, the assessment at step 282 is skipped and, after repositioning the balloon 174 within the prosthetic heart valve 300, inflation liquid is added to the inflate the balloon 174 to further expand the prosthetic heart valve 300 as a matter of standard procedure. For example, in some embodiments an additional amount (e.g., ½ ml or 1 ml) of inflation liquid (in addition to the originally injected amount of inflation liquid) may be added to expand the balloon 174 and the prosthetic heart valve 300 as a matter of standard procedure.

At step 290, the clinician can then proximally retract the medical device delivery system 100 and the guidewire from the patient to complete the method 200. The prosthetic heart valve 300 remains engaged with the annulus of the native aortic heart valve in a functional arrangement.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results.

What is claimed is:

1. A prosthetic heart valve delivery system, the system comprising:
    an elongate catheter comprising: (i) an outer catheter shaft and (ii) an inner catheter shaft extending distally beyond the outer catheter shaft;
    an inflatable balloon member attached at a distal end portion of the catheter; and
    a valve stop member attached to the inner catheter shaft and located within the balloon member,
    wherein the valve stop member comprises a braided body or a cellular body,
    wherein the body of the valve stop member comprises a frustoconical outer profile, and
    wherein the body of the valve stop member further comprises an inverted frustoconical portion located within the frustoconical outer profile.

2. The system of claim 1, wherein the valve stop member comprises the braided body, and wherein the braided body comprises a multi-element braided body.

3. The system of claim 2, wherein the multi-element braided body comprises at least 20 elements that are braided together.

4. The system of claim 1, wherein the valve stop member comprises the cellular body, and wherein the cellular body comprises a laser-cut tube that is shape-set to have a frustoconical outer profile.

5. The system of claim 1, further comprising a nose cone attached to a distal end of the inner catheter shaft.

6. The system of claim 5, wherein a distal end of the balloon member is attached to the nose cone.

7. The system of claim 6, wherein a proximal end of the balloon member is attached to a distal end portion of the outer catheter shaft.

8. The system of claim 1, further comprising a steerable catheter defining a lumen and comprising a pull wire, wherein the catheter is slidably disposed within the lumen.

9. The system of claim 1, wherein a distal end portion of the valve stop member is attached to the inner catheter shaft and a proximal end portion of the valve stop member is slidably coupled to the inner catheter shaft.

10. The system of claim 1, wherein a proximal end portion of the valve stop member comprises a polymeric tube that is slidably coupled to the inner catheter shaft.

11. A prosthetic heart valve delivery system, the system comprising:
    an elongate catheter comprising: (i) an outer catheter shaft and (ii) an inner catheter shaft extending distally beyond the outer catheter shaft;
    an inflatable balloon member attached at a distal end portion of the catheter; and
    a valve stop member attached to the inner catheter shaft and located within the balloon member, wherein the valve stop member defines an internal space within which a portion of the balloon member is located when a prosthetic heart valve is mounted on the balloon member in a position that is distally limited by the valve stop member.

12. The system of claim 11, wherein the valve stop member comprises a braided body or a cellular body.

13. The system of claim 11, wherein a body of the valve stop member comprises a frustoconical outer profile and an inverted frustoconical portion located within the frustoconical outer profile.

14. The system of claim 13, wherein the internal space is defined within the inverted frustoconical portion.

15. A prosthetic heart valve delivery system, the system comprising:
    an elongate catheter comprising: (i) an outer catheter shaft and (ii) an inner catheter shaft extending distally beyond the outer catheter shaft;
    an inflatable balloon member attached at a distal end portion of the catheter shaft, the balloon member having a distal opening with an inner diameter prior to being attached to the distal end portion of the catheter shaft; and
    a valve stop member attached to the inner catheter shaft and located within the balloon member, the valve stop member having an outer diameter that is adjustable between a contracted diameter that is less than the inner diameter and a natural diameter that is greater than the inner diameter.

16. The system of claim 15, wherein the valve stop member comprises a braided body or a cellular body.

17. The system of claim 16, wherein the natural diameter is adjustable to the contracted diameter by longitudinally stretching the braided body or the cellular body.

18. A prosthetic heart valve delivery system, the system comprising:
    an elongate catheter comprising: (i) an outer catheter shaft and (ii) an inner catheter shaft extending distally beyond the outer catheter shaft;
    an inflatable balloon member attached at a distal end portion of the catheter; and
    a valve stop member attached to the inner catheter shaft and located within the balloon member,
    wherein the valve stop member comprises a braided body or a cellular body, and wherein the valve stop member comprises the cellular body, and wherein the cellular body comprises a laser-cut tube that is shape-set to have a frustoconical outer profile.

19. The system of claim 18, wherein the body of the valve stop member further comprises an inverted frustoconical portion located within the frustoconical outer profile.

20. The system of claim 18, further comprising a nose cone attached to a distal end of the inner catheter shaft.

21. The system of claim 20, wherein a distal end of the balloon member is attached to the nose cone.

22. The system of claim 21, wherein a proximal end of the balloon member is attached to a distal end portion of the outer catheter shaft.

23. The system of claim 18, further comprising a steerable catheter defining a lumen and comprising a pull wire, wherein the catheter is slidably disposed within the lumen.

24. The system of claim 18, wherein a distal end portion of the valve stop member is attached to the inner catheter shaft and a proximal end portion of the valve stop member is slidably coupled to the inner catheter shaft.

25. The system of claim 18, wherein a proximal end portion of the valve stop member comprises a polymeric tube that is slidably coupled to the inner catheter shaft.

26. A prosthetic heart valve delivery system, the system comprising:
an elongate catheter comprising: (i) an outer catheter shaft and (ii) an inner catheter shaft extending distally beyond the outer catheter shaft;
an inflatable balloon member attached at a distal end portion of the catheter;
a valve stop member attached to the inner catheter shaft and located within the balloon member; and
a nose cone attached to a distal end of the inner catheter shaft,
wherein the valve stop member comprises a braided body or a cellular body.

27. The system of claim 26, wherein the body of the valve stop member comprises a frustoconical outer profile.

28. The system of claim 27, wherein the body of the valve stop member further comprises an inverted frustoconical portion located within the frustoconical outer profile.

29. The system of claim 26, wherein the valve stop member comprises the braided body, and wherein the braided body comprises a multi-element braided body.

30. The system of claim 29, wherein the multi-element braided body comprises at least 20 elements that are braided together.

31. The system of claim 26, wherein the valve stop member comprises the cellular body, and wherein the cellular body comprises a laser-cut tube that is shape-set to have a frustoconical outer profile.

32. The system of claim 26, wherein a distal end of the balloon member is attached to the nose cone.

33. The system of claim 32, wherein a proximal end of the balloon member is attached to a distal end portion of the outer catheter shaft.

34. The system of claim 26, further comprising a steerable catheter defining a lumen and comprising a pull wire, wherein the catheter is slidably disposed within the lumen.

35. The system of claim 26, wherein a distal end portion of the valve stop member is attached to the inner catheter shaft and a proximal end portion of the valve stop member is slidably coupled to the inner catheter shaft.

36. The system of claim 26, wherein a proximal end portion of the valve stop member comprises a polymeric tube that is slidably coupled to the inner catheter shaft.

37. A prosthetic heart valve delivery system, the system comprising:
an elongate catheter comprising: (i) an outer catheter shaft and (ii) an inner catheter shaft extending distally beyond the outer catheter shaft;
an inflatable balloon member attached at a distal end portion of the catheter;
a valve stop member attached to the inner catheter shaft and located within the balloon member; and
a steerable catheter defining a lumen and comprising a pull wire, wherein the catheter is slidably disposed within the lumen,
wherein the valve stop member comprises a braided body or a cellular body.

38. The system of claim 37, wherein the body of the valve stop member comprises a frustoconical outer profile.

39. The system of claim 38, wherein the body of the valve stop member further comprises an inverted frustoconical portion located within the frustoconical outer profile.

40. The system of claim 37, wherein the valve stop member comprises the braided body, and wherein the braided body comprises a multi-element braided body.

41. The system of claim 40, wherein the multi-element braided body comprises at least 20 elements that are braided together.

42. The system of claim 37, wherein the valve stop member comprises the cellular body, and wherein the cellular body comprises a laser-cut tube that is shape-set to have a frustoconical outer profile.

43. The system of claim 37, further comprising a nose cone attached to a distal end of the inner catheter shaft.

44. The system of claim 43, wherein a distal end of the balloon member is attached to the nose cone.

45. The system of claim 44, wherein a proximal end of the balloon member is attached to a distal end portion of the outer catheter shaft.

46. The system of claim 37, further comprising a steerable catheter defining a lumen and comprising a pull wire, wherein the catheter is slidably disposed within the lumen.

47. The system of claim 37, wherein a distal end portion of the valve stop member is attached to the inner catheter shaft and a proximal end portion of the valve stop member is slidably coupled to the inner catheter shaft.

48. The system of claim 37, wherein a proximal end portion of the valve stop member comprises a polymeric tube that is slidably coupled to the inner catheter shaft.

* * * * *